United States Patent [19]

Woo et al.

[11] Patent Number: 4,965,190

[45] Date of Patent: Oct. 23, 1990

[54] METHODS FOR THE IDENTIFICATION OF MUTATIONS IN THE HUMAN PHENYLALANINE HYDROXYLASE GENE USING DNA PROBES

[75] Inventors: Savio L. C. Woo; Anthony G. Dilella, both of Houston, Tex.

[73] Assignee: Howard Hughes Medical Institute, Coconut Grove, Fla.

[21] Appl. No.: 892,227

[22] Filed: Jul. 31, 1986

[51] Int. Cl.[5] .................... C12Q 1/68; C07H 19/073; C07H 19/173

[52] U.S. Cl. ........................................ 435/6; 435/810; 536/27; 536/28; 536/29; 935/77; 935/78

[58] Field of Search ................ 435/6, 810; 935/77–78; 536/27–29

[56] References Cited

PUBLICATIONS

Kwok et al, Biochemistry, vol. 24, pp. 556–561, 1985.

Chistkons et al, Vopr. Med. Khim., vol. 32, pp. 7–12, 1986.

Botstein et al., Am. J. Hum Genet., vol. 32, pp. 314–331 1980.

Speer et al, Preatal Diagnosis, vol. 6, pp. 447–450 (1986).

*Primary Examiner*—Ronald W. Griffin
*Assistant Examiner*—L. Eric Crane
*Attorney, Agent, or Firm*—Fulbright & Jaworski

[57] ABSTRACT

Disclosed is a method for detection of the mutation in phenylalanine hydroxylase genes. This method can be used for the detection of PKU affected, PKU heterozygotes and normals. Also disclosed are oligonucleotides synthesized to detect the first mutations identified in the human phenylalanine hydroxylase gene. The synthesized probes have base pair mismatches with genomic DNA to facilitate the diagnosis of normal and mutant phenylalanine hydroxylase genes. A simple method for detection of the genetic trait, PKU, without obtaining a previous family history of PKU is provided.

11 Claims, 4 Drawing Sheets

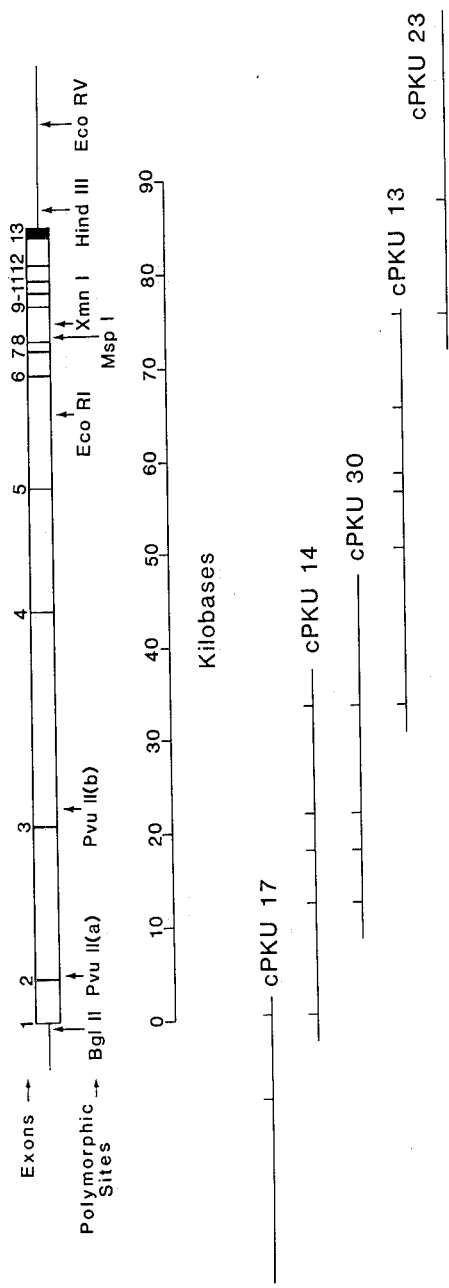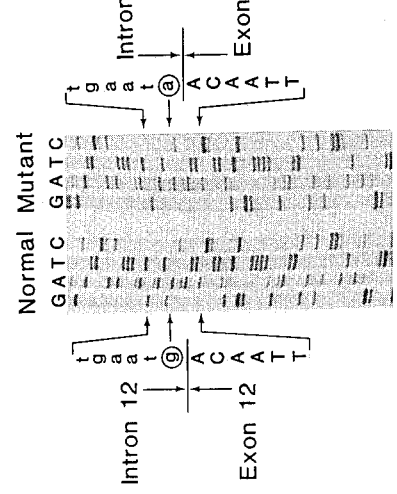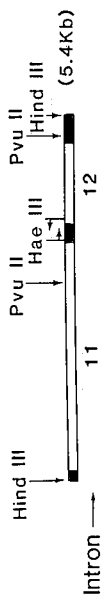
Fig. 1A.
Fig. 1B.

Fig. 2A. PROBE → NORMAL MUTANT
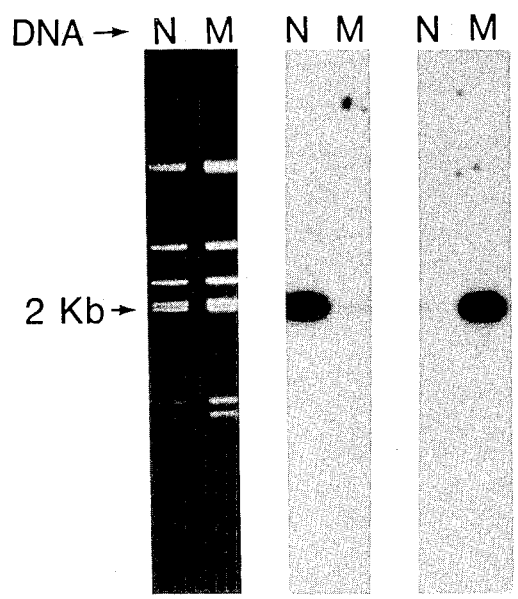
Fig. 2B.
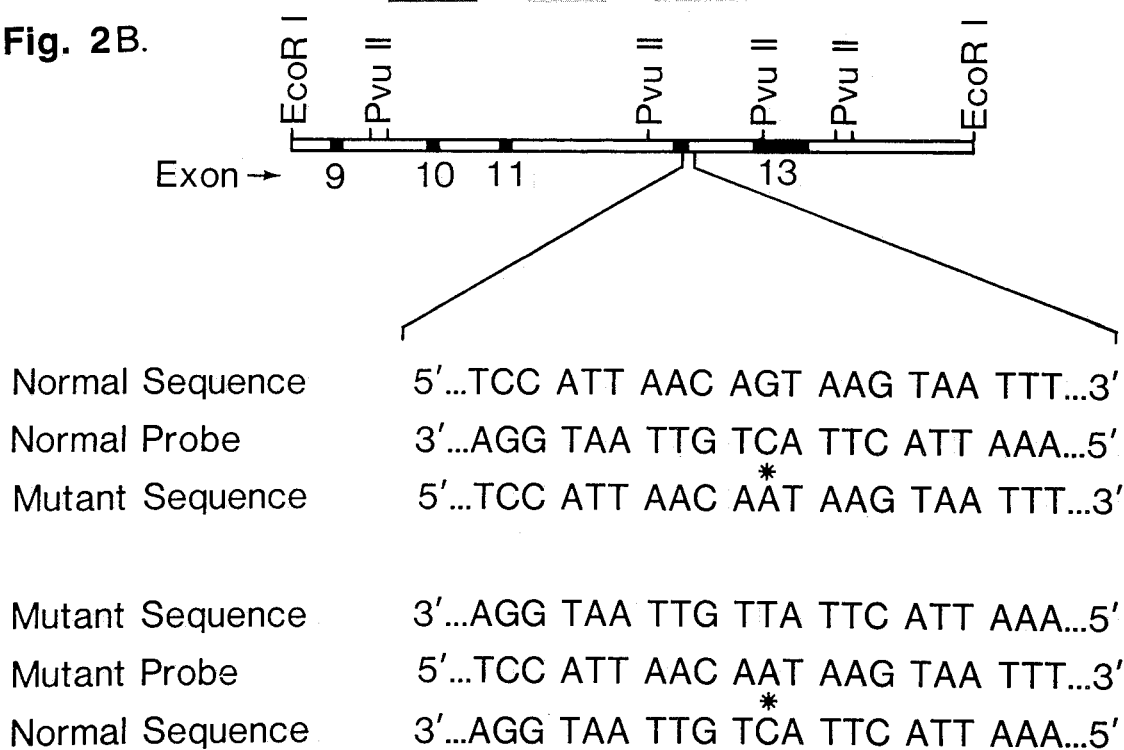
| | |
|---|---|
| Normal Sequence | 5'...TCC ATT AAC AGT AAG TAA TTT...3' |
| Normal Probe | 3'...AGG TAA TTG TCA TTC ATT AAA...5' |
| Mutant Sequence | 5'...TCC ATT AAC A*AT AAG TAA TTT...3' |
| | |
| Mutant Sequence | 3'...AGG TAA TTG TTA TTC ATT AAA...5' |
| Mutant Probe | 5'...TCC ATT AAC AAT AAG TAA TTT...3' |
| Normal Sequence | 3'...AGG TAA TTG T*CA TTC ATT AAA...5' |

A.

```
                                    Amino Acid
                                       #408
                                        ↓
  Mutant      }    Ala  Thr  Ile  Pro  Trp  Pro  Phe  Ser
  Sequence          5'-GCC ACA ATA CCT TGG CCC TTC TCA-3'

Mutant Probe →    3'-G TGT TAT GGA ACC GGG AAG AG-5'
                                       *
  Normal       }   5'-GCC ACA ATA CCT CGG CCC TTC TCA-3'
  Sequence          Ala  Thr  Ile  Pro  Arg  Pro  Phe  Ser Normal       }   3'-CGG TGT TAT GGA GCC GGG AAG AGT-5'
  Sequence Normal Probe →   5'-C ACA ATA CCT CGG CCC TTC TC-3'
                                       *
  Mutant       }   3'-CGG TGT TAT GGA ACC GGG AAG AGT-5'
  Sequence
```

B.

METHODS FOR THE IDENTIFICATION OF MUTATIONS IN THE HUMAN PHENYLALANINE HYDROXYLASE GENE USING DNA PROBES

BACKGROUND OF THE INVENTION

Phenylketonuria (PKU) is a severely handicapping disorder if not diagnosed and treated early in life. PKU is a human genetic disorder caused by an inborn error in aromatic amino acid metabolism. It was first observed some 50 years ago that patients with this condition had excess phenylpyruvic acid in the urine (Folling A., 1934 *Nord. Med. Tidskr*8, 1054–1059; Folling, A., 1934 B, *Zitschr. Physiol. Chem.* 227, 169–176, 1934). Subsequently, it was discovered that livers of such which is the major metabolic pathway of phenylalanine (Jervis, G. A. *J. Biol. Chem.* 169, 651–656, 1947). Clinically, untreated PKU patients present with mental retardation, pigment dilution, hyperkinesis, microcephaly, and seizure activity. However, with the establishment of mass neonatal screening programs (Guthrie and Suzi, *Pediat* 32, 33–34, 1963) and the institution of early dietary therapy (Bickel, H. et al, *Acta Pediat. Scand* 43, 64–77, 1954), the classical clinical presentation is becoming a medical rarity in Western countries. Since mass screening occasionally misses an affected child, follow-up tests of newborns are important. Heterozygote detection followed by genetic counselling of individuals and families with PKU children should guarantee that future children within the families receive these follow-up tests.

Classical PKU is characterized by a lack of phenylalanine hydroxylase activity in the liver. The lack of this enzymatic activity causes persistent hyperphenylalaninemia, resulting in the minor metabolic pathways for phenylalanine becoming over utilized. High levels of phenylalanine and/or its derivatives are toxic and cause disturbances in tyrosine and tryptophan metabolism. Diminished formation of catecholamines, melanin and seratonin is typical in individuals with phenylalanine hydroxylase deficiency. In addition, the melanin sheath surrounding neuronal axons is not properly formed in the brains of untreated PKU patients and the clinical symptoms described above are irreversible.

Phenylketonuria patients secrete large quantities of phenylpyruvate in the urine which can be readily detected by its reaction with ferric chloride. This reaction was used in the 1950's as a screening test for the diagnosis of PKU children. However, in 1962, a simple mass screening method for a semi-quantitative determination of phenylalanine in small samples of blood for newborn infants was subsequently developed by Guthrie and Suzi (*Pediat.* 32, 33–343, 1963). However, individuals diagnosed and treated for classical PKU do not necessarily achieve a normal I.Q. Initiation of dietary therapy soon after birth results in a major disruption of lifestyle and has tremendous psychological and social implications for the patient's family. Dietary regulation must be implemented over a prolonged period of time to be effective and elimination of treatment in the mid first decade is apparently followed by a small but significant decline in I.Q. scores. The supervision of this treatment is difficult and is best performed only at centers experienced with such regimens.

Phenylalanine hydroxylase deficiency, regardless of phenotypic variations, is transmitted as an autosomal recessive trait. Mass screening of over 5,000,000 neonates has shown that the prevalance of classical phenylketonuria in Caucasions ranges from 1/5000 to 1/16000. The collective frequency in western Europe and the United States is about 1/8000 resulting in 2% of the population being heterozygote carriers of the PKU trait.

Many investigators have recognized the need for heterozygosity testing. These tests have involved a variety of methods including using oral phenylalanine loading tests, fasting blood samples in the early morning, semi-fasting mid-day samples, and sophisticated statistical methods for discriminating between heterozygotes and normals. None of the tests that have been developed have a 100% accuracy. All of the tests show some theoretical overlap between heterozyqote and homozygote normal individuals. The main problem is that the measurement of blood phenylalanine is in reality a measurement of secondary phenomena. The enzyme that is deficient, phenylalanine hydroxylase, is only present in the liver. Very few people are willing to give liver biopsies to determine their genetic constitution. Stable isotope analysis is another method used for indirect measurements of this enzyme activity. Phenylalanine is labelled with a non-radioactive $^{13}C$ or $^2H$ and then phenylalanine and its metabolites are measured by mass spectrometry. Again, this is not a direct assay since it measures not only the reaction and conversion of phenylalanine to tyrosine but also the exchange and transport of phenylalanine and tyrosine in the whole body.

With the emergence of molecular biological technology, new methods became available to measure the gene responsible for phenylalanine hydroxylase deficiency and to determine the heterozygosity or genetic state of an individual (Woo, et. al., *Nature* 306, 151–155, 1983, Lidsky, et. al., *Am. J. Human Genet.* 37, 619–634, 1985, and Patent Application Ser. Nos. 484,816 and its continuation-in-part Ser. No. 600,254). These methods of heterozygote detection require the ascertainment of a family through a proband. Furthermore, they require family studies in order to determine the segregation of the PKU alleles with restriction fragment length polymorphisms (RFLP) at the phenylalanine hydroxylase (PAH) locus. Even with family studies, the extensive RFLP's identified in the human phenylalanine hydroxylase locus still leaves some families without a method for detection of heterozygosity or for prenatal diagnosis of affected PKU individuals. The present invention is directed to a new and improved use of molecular biological technology to measure the actual mutations in the PAH locus.

Hydroxylation of phenylalanine to tyrosine involves a complex enzyme system involving at least two enzymes directly and numerous cofactors. Experience over the years has taught that the deficiency exists in more than just the classical PKU state. There is tremendous heterogeniety among the phenotypes and in the hydroxylase deficiency. These include hyperphenylalaninamia, enzyme cofactor deficiencies specifically in the enzyme of dihydropteridine reductase, and cofactor deficiencies. These types of "atypical phenyketonuria" however constitute only a minor percentage of the PKU patients observed. A vast majority of the PKU patients result from a deficiency in the liver enzyme phenylalanine hydroxylase. However, phenylalanine hydroxylase deficiency itself is very heterogenous resulting in diseases ranging from severe, classical PKU, to moderate, hyperphenylalaninemia, states.

The enzyme has been isolated and characterized. It is a multimeric enzyme with a subunit molecular weight of approximately 50,000 daltons. Recent evidence has shown that the subunits are either identical or are precursor - product of one another (Ledley, et. al. *Science* 228 77-79, 1985). In some patients with classical PKU, PAH has been found to exist in a structurally altered form with less than 1% of the normal activity (Bartholome, et al, *Pediat Res.* 9, 899-903, 1975), indicating PKU may be the direct result of a mutation in a PAH gene itself. Furthermore, analysis of PAH activity in liver biopsies of individuals with hyperphenylalaninemia demonstrated that the enzyme contained about 5% of the normal activity level with a range of 2 to 35%. The evidence indicates that the low enzymatic activities of hyperphenylalaninemics are not due to the presence of 5% of the normal enzyme, but rather to the presence of an altered PAH with kinetic properties distinct from both the normal enzyme and the enzyme from patients with classical PKU. These results clearly indicate the presence of multiple phenotypes of PAH deficiency, probably resulting from mutations at various sites in the PAH gene locus.

Phenylalanine hydroxylase cDNA clones have been isolated from rat and human liver cDNA libraries. Our earlier patent applications, Ser. No. 484,816, and Ser. No. 600,254, as well as the publication in *Nature* 306, 151-155, 1983 disclose the use of human PAH cDNA clones representing the 3' half of the PAH messenger RNA(mRNA), to identify RFLP's in the PAH locus in man. The polymorphisms were found using the restriction enzymes MspI, SphI and HindIII and have been applied to trace the transition of the mutant PAH genes in informative PKU families with one or more affected children. These results demonstrated that the mutant PAH genes segregated concordantly with the disease state. The frequencies of the restriction site polymorphism in the PAH gene detected by the partial cDNA clones are such that even under ideal conditions only 70% of the PKU families in the population can take advantage of the genetic analysis. Later studies, patent application Ser. No. 600,254 Kwok, et al, *Biochemistry* 24, 556-561, 1985 and Lidsky, et. al. *Am. J. Human Genet.* 37, 619-634, 1985, describe nucleotide sequence use of a full-length human PAH cDNA clone. Although this significantly increased the number of RFLPs, some families were still unable to utilize this type of genetic analysis.

The new full-length cDNA probe detects six RFLP's that were not previously detected with the 3'-PAH cDNA probe. These additional polymorphisms, representing EcoRI, BglII, XmnI, EcoRV, PvuII(a) and PvuII(b), are mapped and reside within the PAH gene or in the immediate flanking genomic sequences (Di Lella, et. al., *Biochem* 25, 743-749, 1986). The 8 polymorphic restriction enzyme sites in the PAH locus were analyzed in 33 Danish families with at least 1 PKU child. The studies in the Danish population showed a high variability in the number of haplotypes, 12 were found. However, this represents a small number compared to a theoretical value of 1,936 haplotypes. Thus, there is strong evidence indicating a tight linkage of the RFLP's within the gene itself and the presence of linkage disequilibrium. Even with the increased amount of variability, 87%, found in the Danish population with the full-length cDNA and the restriction endonucleases (Daiger et. al., *Lancet* I, 229-232, 1986), there still exist families which cannot utilize this genetic technique. Additionally, the technique has the disadvantage of requiring the ascertainment of a PKU proband before the family can utilize the method. To circumvent these problems, investigations were instituted to identify the specific mutations and to develop methods which detect the specific mutations resulting in altered PAH genes.

SUMMARY OF THE INVENTION

Accordingly, the present invention is directed to design and synthesis of probes which are specific for the mutation that has occurred in the PAH locus. Advantageously, the invention provides a simple method for detection of the genetic trait, PKU, without obtaining a previous family history. It is also directed to the methods of oligonucleotide synthesis and the use of these oligonucleotide probes in the prenatal diagnosis of the human genetic disorder PKU and the detection of carriers of the PAH deficiency trait. The oligonucleotide probes have been used as a hybridization probes to develop an assay to analyze human genomic DNA. The method detects a G (guanine) for A (adenine) substitution at the interface of the intron/exon 12 junction. The Danish population studies demonstrate that PKU is caused by a limited number of mutations and that the majority of the PKU mutations are associated with four common RFLP haplotypes in the PAH gene. The Danish population will be used as a model to develop an assay for the direct analysis of mutation sites in the general population, and thus for the prenatal detection of PKU and the detection of PKU carriers without ascertaining a proband.

The following demonstrates the isolation of a mutant PAH gene corresponding to a predominant PKU haplotype, i.e. haplotype 3, of the Danish population. Sequence analysis showed that a single base substitution occurred in the PAH gene involving an exchange in the 5' donor splice site of intron 12 GT (guanine, thymine) to AT (adenine, thymine). The use of the oligonucleotide probe indicated that the mutation is strongly associated with haplotype 3 which comprises approximately 40% of PKU alleles in the Danish population. Detecting the mutation in other racial and ethnic groups will provide further insights into the evolution and origin of the PKU mutations and haplotypes.

Since the mutation did not result in alteration of the RFLP pattern previously established for the normal PAH gene, the oligonucleotide method is directed to the use of a molecular biological assay for genomic DNA to detect specific mutations.

It is an object of this invention and it is directed to a method of using oligonucleotide probes specific for a genetic mutation in PAH and to determine the heterozygosity state of individuals. Furthermore, it can be used for the prenatal diagnosis and detection of PKU.

A further object of the present invention and it is directed to a diagnostic kit for use in testing for haplotypes and specific mutations of the PAH locus.

Advantageously, this invention can be used and it is an object of the invention to detect mutated PAH in the general population and is not dependent on a proband for utilization of the method in a family.

It is a further object and the present invention is directed to identifying PKU affected fetuses and PKU trait carriers without first ascertaining a proband for utilization of the method in a family.

It is a further object of the present invention to provide and it is directed to a method for the detection of mutations in the haplotypes of PAH gene in the different racial and ethnic populations. This method can be used to identify the origin and trace the evolution of the PAH locus in man. The application of this method will clarify whether PKU was caused by a limited number of mutations that spread throughout the race by founder effect or by multiple PKU mutations arising independently in various population backgrounds.

It is a further object of the present invention and it is directed to a method which provides insight into the evolution and molecular origin of mutations in the PAH gene that cause PKU.

Furthermore, it is an object of the present invention to provide a method directed to identification of PKU heterozygotes and affected PKU's as a preliminary to providing genetic counselling to appropriate individuals.

It is a further object of the invention to provide a simple method for detection of the genetic trait, PKU, without obtaining a previous family history.

It is a further object of the present invention to provide such a method in which, advantageously, the standard molecular biological DNA technology is employed and the components such as the plasmids, etc., are readily available on the market.

Other and further objects, features, and advantages will be apparent from the following description of a preferred embodiment of the invention given for the purpose of disclosure and when taken in conjunction with the accompanying drawings.

DESCRIPTION OF THE DRAWINGS

FIG. 1A is a physical map of the mutant phenylalanine gene in the 5' to 3' orientation. The map was constructed by characterization of five overlapping cosmid clones (cPKU 17, cPKU 14, cPKU 30, cPKU 13, cPKU 23).

FIG. 1B demonstrates the location of the splicing mutation. The sequence analysis of the 5' donor splice site of exon 12 is shown.

FIG. 2A shows the oligonucleotide specificity for the detection of the PKU mutation in cloned DNA by direct gel hybridization. The 2kb PvuII fragment contains exon 12 and flanking intronic sequences. Dried gels were hybridized to oligonucleotide probes specific for normal (N) and mutant (M) genes.

FIG. 2B shows the normal and mutant sequences of the exon/intron 12 border of the phenylalanine hydroxylase gene and the synthesized probes. The astericks represent the mutation location and demonstrate the C-A mismatch on hybridization (A=adenine, T=thymine, G=guanine, and C=cytosine).

DESCRIPTION OF THE PREFERRED EMBODIMENTS INTRODUCTION

Figure 3:
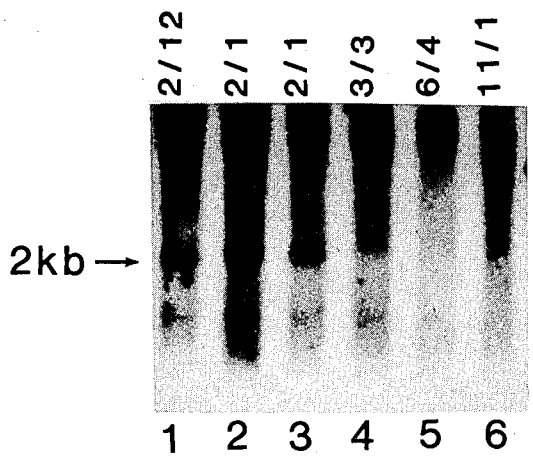
FIG. 3A shows the normal and mutant sequences of the codon mutation associated with the PKU haplotype 2. This corresponds to a substitution of C to T in exon 12 of the PAH gene, and results in the substitution of tryptophan (Trp) for Arginine (Arg) at residence #408 of the protein. The asterisks represent the mutation location and demonstrate the C-A mismatch on hybridization (A, T, G and C are the same as in FIG. 2B).
FIG. 3B shows the mutant probe hybridization in PKU individuals with the haplotype 2 mutation. Lanes 1-3 are individuals with the mutation and lanes 4-6 are individuals without the mutation. The appropriate RFLP haplotypes are shown at the top of each autoradiograph.

The following organisms are available from the permanent collection of the American Type Culture Collection, 12301 Parklawn Drive, Rockville, Md. 20852, U.S.A.

| | |
|---|---|
| ATCC 39644 | E. Coli RR1 (phPAH 247) |
| ATCC 39660 | E. Coli ED8767 (chPAH 15) |
| ATCC 39659 | E. Coli ED8767 (chPAH 10) |
| ATCC 39661 | E. Coli ED8767 (chPAH 14) |
| ATCC 39658 | E. Coli ED8767 (chPAH 25) |
| ATCC 67133 | E. Coli ED8767 (cPKU 23) |
| ATCC 67132 | E. Coli ED8767 (cPKU 1) |

Deposits are available to the public upon a grant of the patent to the assignee, Howard Hughes Medical Institute, disclosing them. It should be understood, however, that the availability of a deposit does not constitute a license to practice the subject invention in derogation of patent rights granted by governmental action.

Restriction fragment length polymorphisms (RFLP) are an example of analysis of human variation of the genotypic level. These polymorphisms can be used much like phenotypic polymorphisms, i.e. electrophoretic variants of proteins to describe the heterogeneity within and between populations. Examples include linkage analysis between a RFLP and a trait of unknown location or the kindered analysis of traits closely segregating or tightly linked to the probe used to identify the RFLP. We have identified many RFLP's in the phenylalanine hydroxylase locus by using full length cDNA as the hybridization probe. These polymorphisms are frequent and suggest a high level of heterozygosity.

Using a human phenylalanine hydroxylase (PAH) cDNA probe to identify and map RFLP's at the PAH locus theoretically should identify a total of 1,936 haplotypes. However, in a study of phenylkentonuria (PKU) in the Danish population, we observed only 12 haplotypes. The 12 haplotypes are defined in Table 1 by these restriction endonuclease sites. The distribution of these haplotypes and the binding to the mutant and normal probes are shown in Table 2. It is clear from Table 2 that although the PKU and normal gene are distributed throughout the haplotypes, the majority of the normal genes are of haplotypes 1 and 4 whereas the majority of PKU genes are haplotypes 1, 2, 3, or 4 with the largest group being of haplotype 3.

TABLE 1

RFLP Haplotypes at PAH Locus from Parental Chromosomes in PKU Families from Denmark

| ID kb length  +  =   − =   * = | BglII 1.7 3.6 | PvuII(a) 6.0 19.0 | PvuII(b) 9.1 11.5 | EcoRI 11.0 17.0 | XmnI 6.5 9.4 | MspI 19.0 23.0 | HindIII 4.0 4.2 4.4 | EcoRV 25.0 3.0 | Frequency in Normal | Frequency in PKU |
|---|---|---|---|---|---|---|---|---|---|---|
| 1  | − | + | − | − | − | + | − | − | 23 | 12 |
| 2  | − | + | − | − | − | + | + | + | 3  | 13 |
| 3  | − | + | − | + | + | − | − | − | 2  | 25 |
| 4  | − | + | − | + | + | − | + | + | 21 | 9  |
| 5  | + | − | + | + | − | + | − | + | 7  | 0  |
| 5  | + | − | + | + | − | + | − | − | 0  | 2  |
| 7  | + | − | − | + | + | − | − | − | 7  | 1  |
| 8  | − | + | − | + | − | + | − | + | 1  | 0  |
| 9  | + | + | − | + | − | + | − | + | 0  | 1  |
| 10 | − | + | − | + | − | + | − | − | 1  | 0  |
| 11 | + | − | − | + | − | + | − | + | 1  | 1  |
| 12 | − | + | − | − | − | + | * | + | 0  | 2  |
| Total | | | | | | | | | 66 | 66 |

The observation of only 12 haplotypes suggests a high degree of linkage disequilibrium between the polymorphic sites. The strong association among the distinct haplotype PKU loci in the Danish population was used to select for a mutant gene for analysis of the defective PAH. In the present application we selected haplotypes 2 and 3 which represent the largest numbers of PKU affected haplotypes and at the same time a very small number of normal alleles.

It is interesting that the majority of the PKU genes in the Danish population are confined to 4 common haplotypes, two of which represent predominantly haplotypes of the normal genes. For example, about 75 percent of the normal PAH genes are confined to haplotypes 1 and 4 (Table 2). A large number of PKU alleles are also associated with these two haplotypes suggesting that the PKU mutation arose on a common haplotype background. About 60 percent of the PKU alleles in the Danish population are represented by two haplotypes, haplotypes 2 and 3 (Table 2). In contrast to the PKU alleles associated with haplotypes 1 and 4, haplotypes 2 and 3 contain few normal alleles. PKU mutations occurring in these haplotype backgrounds could have spread to the Danish population by a founder effect.

Subsequently, we describe the molecular cloning of mutant PAH genes of predominant PKU haplotypes 2 and 3. Sequence analysis of the haplotype 2 gene demonstrates that the mutation site in the gene is identical to that of the normal PAH gene with the single exception of the nucleotide cytosine (C) has been replaced by the nucleotide thymine (T) in exon 12. Similar sequence analysis of the haplotype 3 gene demonstrated that a single base substitution involving the 5' donor splice site of intron 12 was responsible for the mutation in haplotype 3. In this instance, the nucleotide guanine (G) has been replaced by the nucleotide adenine (A). Gene hybridization analysis using the oligonucleotide probes specific for the genetic substitutions demonstrated an absolute association of each mutation with the corresponding PKU haplotype in the Danish population (Table 2). It can be seen that the mutant haplotype 2 probe hybridizes only to the haplotype 2 PKU mutant gene. Additionally the mutant haplotype 3 probe hybridizes only the haplotype 3 PKU mutant gene, whereas the normal haplotype 3 probe hybridizes to all of the other haplotypes, both normal and mutants. The strong association between the haplotype and mutation can be attributed to positive identification for the PKU trait by the probe.

With respect to the Danish PKU haplotype 2 and 3 mutations, several lines of evidence support the founder effect hypothesis to explain the origin of haplotypes of

TABLE 2

Association of PKU Mutation with Mutant Probes in Denmark

| HAPLOTYPE | RFLP ANALYSIS DISTRIBUTION OF ALLELS ANALYZED | | HAPLOTYPE 2 MUTANT PROBE ANALYSIS NUMBER GENES HYBRIDIZED/NUMBER GENES ANALYZED | | HAPLOTYPE 3 MUTANT PROBE ANALYSIS NUMBER GENES HYBRIDIZED/NUMBER GENES ANALYZED | | HAPLOTYPE 3 MUTANT PROBE ANALYSIS NUMBER GENES HYBRIDIZED/NUMBER GENES ANALYZED | |
|---|---|---|---|---|---|---|---|---|
|    | NORMAL | PKU | NORMAL | PKU | NORMAL | PKU | NORMAL | PKU |
| 1  | 23 | 12 | 0/11 | 0/9  | 0/5  | 0/10  | 5/5  | 10/10 |
| 2  | 3  | 13 | 0/2  | 9/9  | ND   | 0/12  | ND   | 12/12 |
| 3  | 2  | 25 | 0/2  | 0/8  | 0/2  | 23/23 | 2/2  | 0/23  |
| 4  | 21 | 9  | 0/1  | 0/4  | 0/6  | 0/8   | 6/6  | 8/8   |
| 5  | 7  | 0  | 0/1  | 0    | 0/1  | 0     | 1/1  | 0     |
| 6  | 0  | 2  | 0    | 0/1  | 0    | 0/2   | 0    | 2/2   |
| 7  | 7  | 1  | ND   | 0/1  | 0/2  | 0/1   | 2/2  | 1/1   |
| 8  | 1  | 0  | ND   | 0    | 0/1  | 0     | 1/1  | 0     |
| 9  | 0  | 1  | 0    | ND   | 0    | 0/1   | 0    | 1/1   |
| 10 | 1  | 0  | ND   | 0    | 0/1  | 0     | 1/1  | 0     |
| 11 | 1  | 1  | ND   | 0/1  | ND   | 0/1   | ND   | 1/1   |
| 12 | 0  | 2  | 0    | 0/2  | 0    | 0/2   | 0    | 2/2   |
|    | 66 | 66 | 0/17 | 9/35 | 0/18 | 23/60 | 18/18 | 37/60 |

ND: Not determined due to lack of DNA samples.

these particular mutations. PKU appears to be predominantly a Caucasian disorder with its gene frequency appearing highest in Ireland and its prevalance progressively decreasing throughout northern and southern Europe. Consequently, it has been postulated that the PKU alleles are of Celtic origin and spread eastward to European populations by the founder principle. The current PAH-RFLP haplotypes established in Denmark are also found in different racial and ethnic groups throughout Europe and the Americas suggesting that the haplotypes originated before the dispersion of the human races. The mutant specific probe thus provides a powerful method to test potential haplotype association of this mutation in various populations. Analysis has shown a close association between the donor splice mutation identified in haplotype 3 and the amino acid substitution mutation in haplotype 2 of the Denmark population. Further studies have also identified the mutations in other Caucasian populations including but not limited to the populations of Switzerland, Scotland, Ireland, England and Italy.

Since phenylalanine hydroxylase is found mainly in the liver, it is not easily accessible for rigorous characterization. Many questions remain unanswered as to the biochemistry of the enzyme. Although PKU has been well characterized clinically, the molecular defect in PAH has not been previously identified. The molecular approach to the study of this inborn error of metabolism was initiated with the cloning of the cDNA for PAH. RFLP's in the chromosomal PAH gene were shown to be useful tools for study in PKU. In the present invention, specific oligonucleotide probes which can distinguish the normal and mutant PAH genes are identified. Unlike previous efforts which required the presence of a probe and family studies to determine the linkage relationships of the mutant gene and the normal gene, the present oligonucleotide probes are used to detect the mutant gene in the general population. The segregation of the mutant haplotype 2 and haplotype 3 genes are distinguishable from their corresponding normal genes in heterozygotes (individuals which carry the mutant and the normal PKU gene) and PKU affected (individuals who have two PKU defective genes).

This analysis requires the collection of DNA material from individuals to be tested. Genomic DNA is isolated from peripheral blood leukocytes. The isolated genomic DNA is the target DNA for the analysis. Similarly, cells can be taken from fetal sources for analysis of DNA. This could include amniotic fluid, fetal biopsy, or chorionic villi.

Cosmid genomic DNA libraries were constructed from isolated leukocyte DNA from PKU individuals homozygous for either haplotype 2 or haplotype 3. The libraries were screened with the full length human PAH cDNA probe, and several corresponding genomic clones were isolated. FIG. 1 shows the EcoRI restriction map of the mutant gene containing 5 overlapping cosmid clones spanning about 135 kb of contiguous genomic DNA. The data demonstrate that PKU is not caused by any obvious deletions within this gene since a similar EcoRI restriction map was made from individuals containing the normal PAH gene.

To identify the mutation, exon containing regions of the mutant genes were subcloned into M13mp18 for sequence analysis. This procedure elucidated the detailed primary structure of 13 exons in the mutant genes.

In FIG. 1B the mutant haplotype 3 pattern is shown for example. The 5-donor splice site of intron 12 was determined on the HaeIII restriction endonuclease fragment containing exon 12 and the downstream intron which was inserted into the SmaI site of M13mp18. The mutant haplotype 3 gene sequence is identical to the normal PAH gene with the single exception of a G to A substitution at the 5' donor splice site of the intron/exon bordor of intron 12. This change alters the obligatory GT donor dinucleotide to AT. Gene transfer and expression experiments demonstrated that this mutation results in abnormal PAH messenger RNA (mRNA) processing and loss in PAH activity. Aberrant RNA splicing causes skipping of exon 12 in the mature mRNA, resulting in translation of a truncated protein product that is unstable in the cell.

The normal specific probe to haplotype 3 was synthesized complementary to the sense-strand of the normal gene (FIG. 2B), and forms a CA mismatch at the mutation site with the mutant gene (FIG. 2B).

For the mutant specific probe an oligonucleotide of the sense strand sequence was synthesized. At the mutation site this probe forms a CA mismatch with the normal gene sequence (FIG. 2B). The specificity of the two oligonucleotide probes to detect respective sequences was then tested using normal and mutant genomic DNA clones. The 12 kb EcoRI fragments isolated from both normal and mutant cosmid clones were inserted into pBR322. Exon 12 plus flanking intronic sequences are contained in a 2 kb fragment after PvuII digestion.

FIG. 2B shows the nucleotide sequence with the mutation site and the oligonucleotide sequences. The substitution of G for A is indicated by the asterisk. Since a single base pair mismatch is sufficient to destabilize the duplex structure in DNA hybrids, oligonucleotide probes can be used to distinguish the mutant and normal alleles in the human genome.

In addition to a G to A transition of the 5' splice donor site of intron 12 of the mutant haplotype 3 gene, a silent nucleotide substitution (A→G) in the third base of codon 232 (Gln) was also detected in this gene. This nucleotide substitution creates a DdeI restriction endonuclease site in exon 6, approximately 13-kb upstream from the splicing mutation in intron 12. This restriction site is not present in the normal phenylalanine hydroxylase gene. If this DdeI polymorphism is in linkage disequilibrium with the allel containing the splicing mutation, it can also be used as a diagnostic test for the mutant phenylalanine hydroxylase allele. This technique does not require the use of the oligonucleotide probes since the mutant-associated RFLP can be detected directly using a cDNA, a genomic DNA or a synthesized oligonucleotide probe. Since only limited sequence analysis has been performed on normal and mutant phenylalanine hydroxylase genes, numerous polymorphisms similar to DdeI potentially exist in regions of the gene that are uncharacterized. If these silent mutations are in linkage disequilibrium with one mutant allele they can provide a method for distinguishing PKU individuals from, heterozygote, and normal individuals.

Mutant haplotype 2 gene sequence is identical to the normal PAH gene with the single exception of a C to T substitution at the codon for amino acid 408 in exon 12. The substitution as shown in FIG. 3A results in a change from a CGG triplet to a TGG triplet. This single base change in the triplet results in the coding for a different amino acid. The normal sequence codes for the amino acid arginine. The mutant sequence codes for the amino acid tryptophan. Mutant specific probe synthesized complementary to the sense-strand of the mutant gene forms a C-A mismatch at the mutation site of the normal gene. Similarly a normal probe was synthesized as the sense strand of the normal gene. In FIG. 3A we see that this forms a C-A mismatch at the mutation site of the mutant gene sequence.

The fidelity of the mutant and normal probes to detect the corresponding mutant and normal sequence was verified using the normal and mutant genomic DNA clones. The 12 kb EcoRI fragments isolated from both normal and mutant DNA clones were inserted to pBR322. The mutation site and corresponding flanking sequences are contained in a 2 kb fragment after PvuII digestion.

Due to the high AT content of the normal and mutant probes used for analysis of the heplotype 3 mutation, the base composition independent oligonucleotide hybridization method was utilized in analyzing the point mutation. Under these conditions, the normal probes hybridized only with the 2 kb PvuII fragment of the normal genes and the mutant probes hybridized specifically to the mutant genes (FIG. 2A for haplotype 3 and FIG. 3B for haplotype 2). Thus, the synthetic oligonucleotide probes are useful in identifing the mutant alleles in genomic DNA of PKU affected and heterozygotes in the population and to determine the segregation pattern in PKU kindreds.

To verify that the mutations were not constitutive parts of normal haplotype alleles, PKU families containing the same normal and mutant haplotype alleles were analyzed. Individuals containing both the normal and mutant haplotype alleles hybridize both probes, individuals with the normal haplotype hybridize only the normal probe and individuals with the mutant haplotype hybridize only the mutant probe. Table 2 shows the specificity of the probes. The mutant haplotype 2 probe bound only to mutant haplotype 2 alleles the mutant haplotype 3 probe bound only to the mutant haplotype 3 alleles. The normal probes bound to all haplotypes except their corresponding mutant gene haplotype. Only the data for the normal haplotype 3 probe is shown but similar results were obtained using the normal haplotype 2 probe. Thus, both the splicing mutation of haplotype 3 and the amino acid substitution mutation of haplotype 2 are not constitutive parts of their respective normal haplotye alleles. Similarly, the mutant probe was hybridized to PKU families containing other mutant alleles. The mutant probes did not hybridize to the DNA isolated from these individuals. These data (Table 2) indicate that the PKU mutation associated with alleles other than haplotypes 2 and 3 are not the same mutations and are consistent with the theory of heterogeneity of origin of PKU diseases. The results suggest that each haplotype may contain its own individual mutation. Further experiments will determine these specific mutations associated with haplotypes other than haplotypes 2 and 3.

MATERIALS AND METHODS

Advantageously, standard chemical materials were used in this invention. Sources and materials include cosmid vector pCV107 and E.Coli strains (donated by Y. F. Lau and Y. W. Kan of the University of California at San Francisco), restriction endonucleoses (New England Biolabs), M13mp18 and dideoxynucleotide sequencing kit supplies (P-L Biochemicals), radionucleotides (Amersham Corp.), tetramethylammonium chloride (Aldrich) and autoradiography supplies (DuPont and Kodak).

THE RECOMBINANT COSMID CLONES

Cosmid genomic libraries were constructed from lymphocyte DNA isolated from two PKU individuals homozygous for haplotypes 2 and 3. The libraries were screened with phPAH247 which is a full-length human PAH cDNA probe as was previously described for the normal gene (DiLella, et. al. *Biochem.* 25, 743–749, 1986) and the corresponding genomic sequences were isolated from a number of positive clones. For haplotype 3, cosmid clones cPKU 17, cPKU 14, cPKU 30, cPKU 13, and cPKU 23 contain various portions of the human chromosomal PAH gene identified from the genomic DNA library constructed using the cosmid vector pCV107 according to Lau and Kan (*Proc. Nat'l Acad. Sci. U.S.A.* 80, 5225–5229, 1983). Southern hybridization indicated that the clones cPKU 17, cPKU 14, and cPKU 30 contain the 5 portion, cPKU 30 and cPKU 13 contain the middle portion and cPKU 13 and cPKU 23 contain the 3' portion of the gene. The five overlapping cosmid clones span about 135 kb of contiguous genomic DNA containing the PAH locus. For haplotype 2, cosmid clones cPKU 13 and cPKU 1 contained portions of the human PAH gene. Southern hybridization indicated that clone cPKU 1 contained exons 8 to 13, whereas clone cPKU 13 contained exons 6 to 13.

SEQUENCING OF THE MUTANT AND NORMAL GENES.

For haplotype 3, five overlapping cosmid clones (cPKU 7, cPKU 14, cPKU 30, cPKU 13 and cPKU 23) were used to characterize the mutant gene. For haplotype 2, two overlapping cosmid clones (cPKU 13 and cPKU 1) were used to characterize the mutant gene. Subcloned EcoRI fragments containing the specific exon sequences were used for Sanger-Dideoxynucleotide sequence analysis as described in Sanger, et. al. *PNAS* 74, 463–5467, 1977.

DIRECT-GEL HYBRIDIZATION

The 12 kb EcoRI fragment containing exons 9–13 was isolated from normal and mutant cosmid clones for either haplotypes 2 or 3 and inserted into pBR322. The subcloned EcoRI fragment, or total human genomic DNA were digested and PvuII electrophoresed on 1% agrose gels, stained with ethidium bromide and processed for direct-gel hybridization as described in Kidd et al *Nature* 304, 230–234, 1983. Dried gels were hybridized to oligonucleotide probes specific for normal and mutant PAH genomic DNA sequences. Exon 12 plus some flanking intronic sequences are contained in the 2 kb PvuII fragment. The dried gels are hybridized overnight at 37° C. in 6xNET (0.9M NaCl, 6 mM EDTA, 0.5% SDS and 0.09M Tris, pH 7.5) containing 0.2 mg of salmon sperm DNA and $2 \times 10^6$ cpm of probe per ml of hybridization solution. The gels were then washed as described by Wood, et. al. *PNAS* 82, 1585–1588, 1985 with modification as follows: twice at 0° C. for 30 minutes in TMA (3M tetramethylammoniumchloride, 2 mM EDTA and 50 mM Tris, pH 8.0), once each at 23° C. (30 minutes) and 60° C. (7 minutes) in TMA containing 0.2% SDS and 23° C. for 30 minutes in TMA. The gel strips were then autoradiographed between two Quanta III intensifier screens at −80° C.

DOT BLOT AND SLOT BLOT ANALYSIS

Analysis of genomic DNA by dot blot hybridization has facilitated the identification and dosage of specific sequences within the human genome. In the dot blot technique, total genomic DNA is applied directly to nitrocellulose or other membranes without prior treatment with restriction endonucleases. Multiple DNA samples are applied onto the membrane. The need to separate digested DNA fragments by agarose gel electrophoresis along with Southern transfer of DNA from agarose gels onto nitrocellulose is alleviated.

In the slot blot technique, total genomic DNA samples are immobilized in a slot configuration resulting in a greater concentration of nucleic acid per unit area of membrane.

In both the dot blot and slot blot techniques, the total genomic DNA is denatured by standard methods: for example, heating at 100° C. for 10 minutes in 50 microliters containing 10 mM Tris, 1 mM EDTA (pH 8.0), quick cooled in ice, and diluted two fold with 20 × SSC. Samples are applied to nitrocellulose or other membrane in a dot blot or slot blot manifold filtration device according to manufacturer specifications (Schleicher and Scheull). Hybridization is the same as used in the dried-gel method.

POLYMERASE CHAIN REACTION METHOD

Point mutations causing genetic disorders can be detected by the ploymerase chain reaction (PCR) procedure (R. Saiki et al. Science 230:1350, 1985). In this method, a nucleic acid sequence ca be exponentially amplified in vitro. Human genomic DNA is denatured in the presence of a large molar excess of two oligonucleotides and the four deoxyribonucleoside triphosphates. The oligonucleotides are complentary at relative positions on the sense and antisense strands of DNA flanking the mutation sequence. Under these conditions, the DNA polymerase extension product of the first oligonucleotide can serve as a template for the second oligonucleotide, and vice versa.

A microgram of human DNA contains $5 \times 10^{-19}$ moles of each single copy sequence. For the human PAH gene, a 20-cycle PCR would result in a 200,000 fold increase in the level of exon 12 (116 bp) representing 0.1 pmoles of amplified fragment. In 1 microgram of unamplified genomic DNA, exon 12 plus neighboring sequences represent about 50 femtograms of DNA. When the same quantity of DNA is amplified using the PCR procedure, however, the levels of exon 12 plus neighboring sequences approach 10 nanograms. This increase in quantity allows the oligonucleotide probe to be significantly smaller, since non-specific background binding will not interfere with interpretation of binding results. Thus it is not necessary that the probe be a unique individual sequence.

Oligonucleotides are designed to produce an amplified fragment containing the exon 12 point mutation (C to T) at codon 408 (haplotype 2) or the donor splice mutation (G to T) of intron 12 (haplotype 3). For the haplotype mutations, an oligonucleotide complementary to the sense or antisense strand of intron sequences downstream of the slicing mutation is utilized. The second oligonucleotide is made complementary to the product of the first oligonucleotide and can contain exonic or intronic sequences upstream of the splicing mutation. For the haplotype 2 mutation, an oligonucleotide complementary to the sense or antisense strand of exon or intron sequences downstream of the point mutation is utilized. The second oligonucleotide is designed complementary to the product of the first oligonucleotide and can contain exonic or intronic sequences upstream of the point mutation.

One microgram of human DNA, 1 uM of each oligonucleotide and 1.5 mM of each deoxynucleotide triphosphate in 10 mM tris-chloride, pH7.5, 50 mM sodium acetate, and 10 mM magnesium chloride is heated at 100° C. for 5 minutes and cooled in an ice bath. Five units of Klenow fragment is added and the reaction is incubated at 25° C. for 2 minutes. The cycle of heating, cooling, adding enzyme and reacting is repeated twenty times. The reaction is then applied to a nitrocellulose filter or other membrane using the slot-blot or dot-blot technique as described previously. The mutant sequence can then be detected by any of the described methods in this patent. The PCR technique circumvents the need to analyze point mutations by gel electrophoresis or restriction enzyme digestion. Furthermore the specific oligonucleotide probes can be very short because of the 200,000 fold increase in sensitivity over background.

This increase in sensitivity also allows the use of either DNA strand for the detection of the mutations. Normally, the preferred DNA strand is the one which forms a C-A mismatCh. The G-T mismatch shows some complementation and thus is not as efficient in detecting the mutation. However, the amplification of the DNA sequences increases the sensitivity approximately 200,000. Under these conditions the G-T partial complementation does not interfere with the detection of the mutation. The G-T mismatch can be detected because of the increased sensitivity.

Both the PCR technique and dot-blot/slot-blot methodology using specific oligonucleotides can be readily automated to carry out mass-screening of PKU carriers. Automation is achieved by utilization of currently available commercial instruments for the different steps.

Various instruments are available for the automated amplification of DNA sequences. These instruments will be linked to commercially available automated sequence synthetic machines. Samples can be automatically removed from the synthesis machines, digested, and applied to a dot-blot or slot-blot detection system. Since these are commercially available instruments for all the steps, an integrated system can be provided. The major advantage of an integrated system is cost efficiency. With automation each individual analysis becomes relatively inexpensive. Reginal laboratory systems, similar to those that have developed for newborn screening, can be implemented. Thus, as probes are developed to detect genetic disorders, the system can be expanded. It is contemplated that heterozygote detection will become a routine procedure. As the number of individuals tested and the diseases tested increase, the cost per unit decreases such that it becomes relatively inexpensive. Since each genetic mutation tested will have a specific sequence, multiple tests can be run. In the amplification procedure multiple starter sequences can be added. Each sequence will be amplified. It is then a simple matter to use the specific probes to dissect the genome of an individual. With the system, a single sample can be analyzed for a number of genetic disorders. For example and not limitation, the system can detect cystic fibrosis, Huntington's chorea, muscular dystrophy, phenylketonuria, hemoglobin disorders and Tay-Sachs and other genetic disorders. One skilled in the art will quickly recognize that once a probe is developed it can be quickly integrated into the automatic screening procedure.

Results

Multiple Restriction Fragment Length Polymorphisms in the Human PAH Locus

High molecular weight genomic DNA isolated from peripheral leukocytes of Danish PKU families and Caucasian normal individuals were digested with a number of restriction enzymes followed by Southern blot analysis. Although many restriction enzymes will work we chose the following enzymes for the analysis: BglII, PvuII(a), PvuII(b), EcoRI, XmnI, MspI, HindIII, and EcoRV. These enzymes are not to be considered exhaustive or limiting but rather examples of the enzymes which are readily available.

EcoRV: EcoRV digestion results in 3 invarient fragments and a fourth allelic fragment of either 30 kb or 25 kb. Individuals homozygous (have the two genes) for the 30 kb fragment lack the polymorphic EcoRV restriction site and those homozygous for the 25 kb fragment have the polymorphic EcoRV site in each of their phenylalanine hydroxylase genes. Heterozygotes (individuals who contain one gene with 25 kb and one gene with 30 kb fragments) for the restriction sites in these chromosomes have also been detected.

HindIII: The HindIII site polymorphism has 3 allelic forms of 4.4, 4.2 and 4.0 kb fragments due to the insertion/deletion of a 0.2 kb DNA unit.

MspI: The MspI polymorphism in the PAH gene consists of two alleles, 23 kb and 19 kb.

XmnI: The XmnI polymorphic restriction fragments are 6.5 kb and 9.4 kb.

EcoRI: EcoRI analysis showed the existance of two allelic forms resulting in 11 kb and 17 kb fragments.

PvuII: Digestion with PvuII shows 4 fragments of variable length created by 2 polymorphic PvuII restriction sites. The 4 fragments segregate as 2 separate sets of alleles and the two polymorphic sites are designated (a) and (b). The presence of site (a) results in the cleavage of a 19 kb fragment into 2 fragments of which only the 6 kb fragment hybridizes. The second site (b) results in the cleavage of the 11.5 kb fragment into a 9.1 hybridizable fragment. There can be a total of 10 possible haplotype combinations between the two sets of alleles in an individual.

BglII: The BglII polymorphic site in the PAH gene results in restriction fragments of either 3.6 or 1.6 kb.

SYNTHESIS OF THE OLIGONUCLEOTIDES

The oligonucleotides were synthesized by an automated (SYSTEC, Inc.) solid-phase phosphite triesther method. High specific activity probes (i.e., $10^{10}$ cpm/ug) were generated by the primer extension method of Studencki, et. al. *DNA* 3, 7–15, 1984. The probes were synthesized on a template by the extension of a hybridized base primer. Although probes as small as 15 nucleotides have been used, the preferred embodiment is a 21 nucleotide probe. As an example of the preferred embodiment, the normal haplotype 3 probe was synthesized on a 21 base template (5'-TCC ATT AAC AGT AAG TAA TTT-3') by the extension of a hybridized 9 base primer (3'-TTC ATT AAA-5'). The mutant haplotype 3 probe was synthesized on a 21 base template (3'-AGG TAA TTG TTA TTC ATT AAA-5') by extension of a hybridized 9 base primer (5'-TCC ATT AAC-3'). Similar base primers and extension was used to synthesize the haplotype 2 probes. Experience teaches that probes of at least 15 nucleotides are needed to specifically detect point mutations in human genomic DNA. In the preferred mode, the synthesis provided a normal haplotype 3 probe which was 3'...AGG TAA TTG TCA TTC ATT AAA...5', a mutant haplotype 3 probe which was 5'... TCC ATT AAC AAT AAG TAA TTT...3', a normal haplotype 2 probe which was 5'... C ACA ATA CCT CGG CCC TTC TC...3' and a mutant haplotype 2 probe which was 3'... G TGT TAT GGA ACC GGG AAG AG... 5'. These probes were used for hybridization studies to determine the specific binding with the target DNA from the individuals being examined. One skilled in the art will recognize that probes to the complementary can also be synthesized starting with the appropriate primers and template strands.

MUTATION SEQUENCES

The 114 kb HaeIII fragment isolated from mutant haplotype 3 cosmid clone cPKU23 containing 90 b.p. of exon 12 and 24 b.p. of the downstream intron were inserted into the SmaI site of M13mp18 (Messing, *Methods Enzymol.* 101, 20–78, 1983). These were then sequenced by the dideoxynucleotide chain termination method as per Sanger, et. al., *PNAS* 74, 5463–5467, 1977. A comparison of the normal and mutant sequences of the intron/exon border demonstrates that a single base substituion of A for G is the only distinction.

Similarly, the 2kb PvuII fragment isolated from mutant haplotype 2 cosmid clone cPKU1 containing exon 12 was inserted into the SmaI site of M13mp18. Dideoxynucleotide chain termination sequence analysis was performed using oligonucleotide primers specific for the intronic sequences flanking exon 12. The sequence analysis for haplotype 2 demonstrated a C to T substitution at the condon for amino acid 408 in exon 12. The substitution results in a change from CGG to a TGG triplet.

PROCEDURE FOR PRENATAL DIAGNOSIS OF PKU AND HETEROZYGOTE (CARRIER) DETECTION USING THE SPECIFIC PROBES

The following example is a summary of procedures to be followed to detect the presence of the mutant genes for prenatal diagnosis or heterozygote detection:

1. A sample is obtained from the individual to be tested. The sample can include but is not limited to the following: Venus blood sample, amnionic fluid, chorionic villi, human tissue and dried blood spot.
2. Genomic DNA in a biological sample is digested to completion with PvuII restriction enzyme. This digested genomic DNA becomes the target DNA. This target DNA can be amplified by the PCR technique.
3. The digested target DNA is directly applied to membranes or the fragments are separated by agarose gel electrophoresis and applied to membranes.
4. Analyze the digested target DNA by the dry-gel, dot blot, or slot blot hybridization procedure described previously with normal- and mutant-specific oligonucleotide probes.
5. Identify the hybridization fragments to distinguish the normal from the mutant PAH genes. Homozygous normal individuals will hybridize only with the normal oligonucleotide probes. Heterozygote individuals containing a mutant haplotype 2 or 3 allele will hybridize with both the normal and one of the mutant oligonucleotide probes and affected PKU individuals homozygous for either mutant allele will hybridize only with the respective mutant oligonucleotide probe. PKU individuals who are heterozygous for the two mutant alleles are "compound heterozygotes" and will hybridize with both mutant oligonucleotides as well as the corresponding normal oligonucleotides.

Using the PCR technique, amplified DNA can be used in these steps. This provides the opportunity to automate the system and to use the dot-blot or slot-blot techniques to their best advantage.

In the case of individuals who are alive, the preferred tissue is a dried blood spot or venus blood. For carrier detection, genomic DNA isolated from blood can be analysed directly. For prenatal detection of the mutant alleles, fetal samples can be obtained either by amniocentesis followed by collection of the amnionic cells or alternately fetal chorionic villi can also be used as a source of the target DNA. The amniocentesis procedure is used routinely in major hospitals with prenatal diagnosis centers and the chorionic villi procedure is increasing in use. The procedure utilizes either the haplotype 2 or 3 probes or a combination of both haplotype 2 and 3 probes.

Diagnostic Kit

The oligonucleotide probes of this invention are suitable for use in diagnostic kits consisting of the normal oligonucleotide and the mutant oligonucleotide probes. The presence of the probes can be detected by any suitable method available. This can include but is not limited to autoradiographic, photographic, fluoresent or colorimetric measurements. An outside source of target DNA is added to the kit's ingredients. The kit preferably includes synthesized oligonucleotides for all of the identified PKU mutations and the corresponding normal oligonucleotides. However various subcombinations will also be effective.

Oligonucleotide Specificity

The mutations did not result in alterations of known restriction recognition sequences. (DiLella, et. al *Biochem.* 25, 743–749, 1986). The molecular defects in the genomic DNA were then assayed using synthesized oligonucleotide probes. Since a single base pair mismatch between the synthetic probe and the complementary genomic DNA sequence is sufficient to cause instability of the duplex structure in the DNA hybrid, the oligonucleotide probes can be used to distinguish between normal and mutant PAH alleles in the human genome. The oligonucleotide probes were designed according to the principles used to detect point mutations. (Kidd, et. al, *Nature* 304, 230–234, 1983). The synthesized probes used to analyze PKU mutations in the cloned genomic DNA are shown in FIG. 2B (haplotype 3) and FIG. 3A (haplotype 2). Table 2 shows that the mutant oligonucleotide probe to haplotype 3 only hybridizes to the haplotype 3 PKU mutant genes. Similarly the haplotype 2 oligonucleotide probe only hybridizes to the haplotype 2 PKU mutant genes. The mutant specific probes in the preferred embodiment are 21 base oligonucleotides synthesized as the sense-strand sequence of the mutant gene (haplotype 3) or complementary to the sense-strand (haplotype 2). At the haplotype 3 mutation site, the mutant probe forms a stable A-T base pair with the anti-sense strand of the complementary mutant genomic DNA sequence and a C-A mismatch with the normal-complementary genomic DNA sequence (FIG. 2B). In the haplotype 2 mutation site the mutant probe forms a stable A-T base pair with the sense-strand of the mutant genomic DNA sequence and a C-A mismatch with the normal-complementary genomic DNA sequence (FIG. 3A).

On the other hand, the normal haplotype 3 specific probe is a 21 nucleotide chain synthesized complementary to the sense-strand sequence of the normal gene. The C residue at the intron/exon junction of the oligonucleotide probe forms a stable C-G base pair with a normal sense-strand genomic sequence. In contrast, the normal haplotype 3 specific oligonucleotide sequence forms a C-A mismatch at the mutation site in the mutant sense-strand genomic DNA. Thus, the synthesized probe and methods used can detect a single mutation at the intron/exon 12 junction. Under the conditions described above, the normal probe hybridizes spechfically to the 2 kb PvuII fragment of normal gene and the mutant probe hybridizes specifically to the 2 kb PvuII fragment of mutant genes. The PvuII fragments can be used for analysis of both haplotype 2 and 3 mutations and are for example only. Any restriction fragment which preserves the haplotype 2 and 3 mutation sites will work equally well with the probes developed in this invention.

FAMILY STUDIES

Figure 4A:
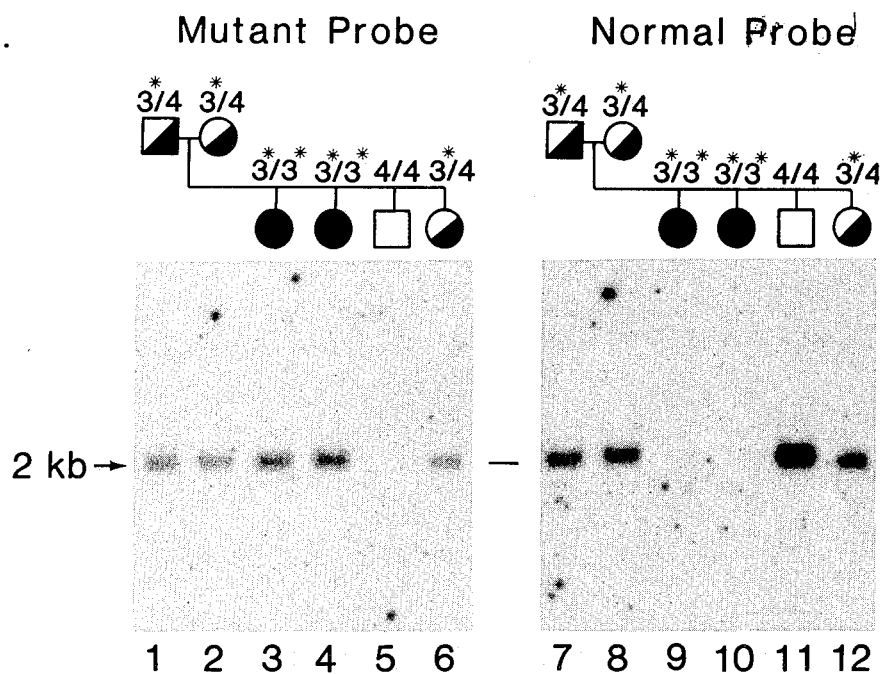
FIG. 4A shows oligonucleotide hybridizaton analysis of a PKU family containing mutant haplotype 3 alleles. Lanes 1 and 7, father; lanes 2 and 8, mother; lanes 3, 4, 9, and 10, two affected children; lanes 5, 6, 11, and 12, two unaffected children. The segregation of the PKU alleles (*) and the appropriate RFLP haplotypes are shown at the top of each autoradiograph.

The synthetic oligonucleotide probes were used to identify the mutant alleles and genomic DNA of PKU patients and family members in PKU kindreds. This further analysis establishes the Mendelian segregation pattern of the mutant gene fragments. The first family analyzed was the one from which the mutant haplotype 3 allele was isolated and characterized. In this family, both parents contained the mutant haplotype 3 PAH gene which hybridized to the mutant-specific probe. FIG. 4A, lanes 1 and 7 is the father, lanes 2 and 8 the mother, lanes 3, 4, 9 and 10 two affected children, and lanes 5, 6, 11 and 12 two unaffected children. In this family both parents contain the mutant haplotype 3 gene which hybridize the mutant probe (FIG. 4A, lanes 1 and 2) suggesting that both mutant alleles in this family contain the same mutation. Since the disorder is autosomal recessive in nature, both parents are obligate carriers of the PKU trait and hence each must also contain a normal gene. In this case both normal alleles in the two parents correspond to the haplotype 4 and as expected both hybridize to the normal probe (FIG. 4A lanes 7 and 8). There are two affected inviduals in this family. Both are homozygous for the mutant haplotype 3 alleles which hybridize strongly to the mutant probe (FIGS. 4A lanes 3 and 4) and not at all to the normal probe (lanes 9 and 10). These results confirm that both mutant alleles in this family contain the same mutation. An unaffected sibling in this family is homozygous for the normal haplotype 4 alleles which hybridize only the normal probe (FIG. 4A lane 11) and not to the mutant probe (lane 5). An unaffected sibling in this family who is heterozygous for mutant haplotype 3 and normal haplotype 4 alleles hybridizes to both the mutant and normal probes (FIG. 4A, lanes 6 and 12, respectively). Thus, the oligonucleotide data not only detected the specific mutated genomic DNA, but also demonstrated the concordant segregation of the normal and mutant alleles in this PKU family.

Figure 4B:
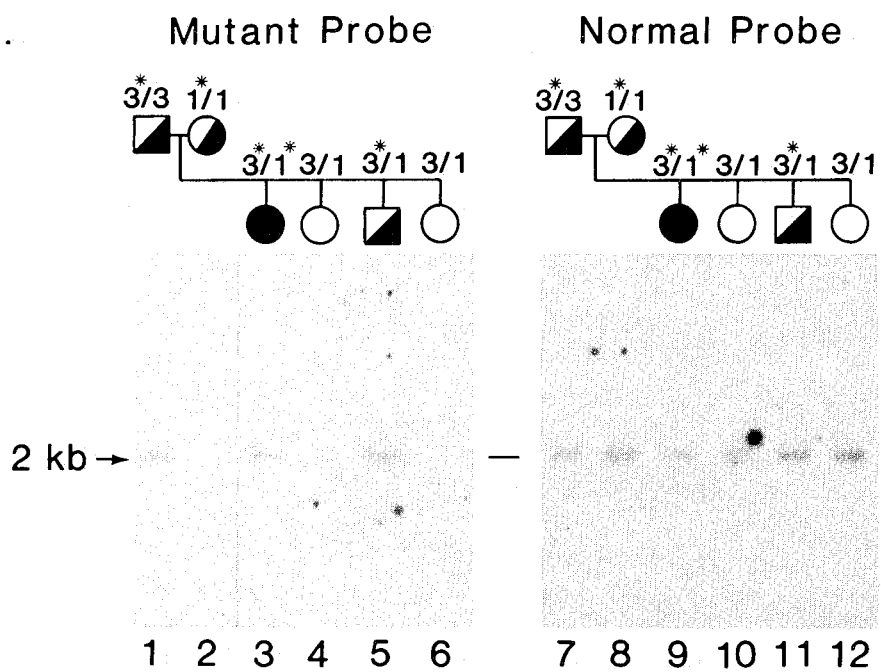
FIG. 4B shows oligonucleotide hybridization analysis of a PKU family with different mutations (i.e., mutant haplotype 3 and haplotype 1 alleles). Lanes 2 and 8, mother; lanes 1 and 7, father; lanes 3 and 9, proband; lanes 4-6 and 10-12, three unaffected individuals. The segregation of the PKU alleles (*) and the appropriate RFLP haplotypes are shown at the top of each autoradiograph.

An additional PKU family containing both normal and mutant haplotype 3 alleles was analyzed. In FIG. 4B lanes 2 and 8 are the mother, lanes 1 and 7 father, lanes 3 and 9 proband, and lanes 4-6 and 10-12 three unaffected individuals. The father in this family was homozygous for haplotype 3 and is an obligate carrier for the PKU trait. The father contained a mutant haplotype 3 allele which hybridized with the mutant probe (FIG. 4B lane 1) and a normal haplotype 3 allele which hybridized the normal probe (FIG. 4B lane 7). These results demonstrate conclusively that the splicing mutation is not a constitutive part of the normal haplotype 3 alleles per se. In contrast, the mother contained the normal and mutant haplotype 1 PAH alleles. The mutant probe did not hybridize to the target DNA isolated from this individual (FIG. 4B lane 2) while the normal probe did hybridize (lane 8). This strongly indicates that the PKU mutation associated with the haplotype 1 alleles is not the same mutation identified in the mutant haplotype 3 alleles. The proband who had an inherited mutant haplotype 3 allele from the father and a mutant haplotype 1 allele from the mother hybridized to both the mutant and normal probes (FIG. 4B lanes 3 and 9, respectively). The splice mutation was associated with the mutant haplotype 3 alleles in three unrelated individuals, i.e., mother and father (FIG. 4A) and father (FIG. 4B) and in observations of analysis in five additional PKU families. The data provides strong genetic evidence that the mutation of the intron/exon 12 junction is associated with the haplotype 3 allele. Further evidence shown in Table 2 established that of all the individuals tested with the specific mutant oligonucleotide probe only those who had the haplotype 3 mutation hybridized to this probe. Additionally, PKU individuals who have mutations on non-haplotype 3 alleles do not hybridize to this probe. On the other hand, the normal oligonucleotide hybridized only to individuals who had a normal sequence at this location on the gene locus.

Similar results are shown in FIG. 3B using the haplotype 2 mutant probe. Those PKU individuals with a haplotype 2 allele (lanes 1, 2, and 3) bind to the mutant probe while PKU individuals with mutations on non-haplotype 2 alleles (lanes 4, 5, and 6) show no binding to the mutant probe.

These data indicate that PKU results from different mutations at different locations in the PAH gene. Thus, the mutations associated with different haplotypes may result in the requirement of specific oligonucleotides for each mutation location. Although the identification of the mutations in the PKU genes of other haplotypes has not yet been achieved at this point, it is postulated that PKU genes of haplotypes 1 and 4 would also be in linkage disequilibrium with a limited number of mutant alleles. Once these mutations become established, the corresponding mutations can be identified in genomic DNA of random individuals by oligonucleotides hybridization technology as described here for haplotypes 2 and 3. If the mutations involve a change of restriction sites, they can also be directed by regular RFLP analysis using a cDNA probe or a corresponding genomic DNA probe in a manner similar to that described for detection of the sickle cell gene. Since haplotypes 1 to 4 constitute 90% of mutant alleles contributing to PKU in Caucasions of Northern European ancestry, it will be possible to perform carrier detection of PKU for this population with an accuracy of 90%. Since the same mutant alleles are also detected in Caucacians of other ethnic backgrounds, the method is applicable to the Caucasian race in general. As more mutant alleles become characterized at the molecular level, additional probes will be designed for their detection in the population. Consequently, the accuracy of the carrier detection method disclosed here will continue to increase in the future.

The present invention therefore is well adapted to carry out the objects and attain the ends and advantages mentioned as well as those inherent therein. Presently preferred embodiments of the invention have been given for the purposes of disclosure and changes and modifications can be made which will readily suggest themselves to those skilled in the art and which are encompassed within the spirit of the invention and the scope of the appended claims.

What is claimed is:

1. A method for detecting PKU affected, PKU heterozygotes and normals in fetal to adult human samples comprising:

analyzing the phenylalanine hydroxylase gene from samples utilizing the methods of hybridizing oligonucleotides to DNA from such samples.

2. The method of claim 1 wherein the gene analysis comprises:

(a) hybridizing an oligonucleotide specific to a mutant sequence of a human phenylalanine hydroxylase gene;

(b) hybridizing an oligonucleotide specific to the normal sequence of the human phenylalanine hydroxolase gene; and (c) determining the binding of the oligonucleotide of (a) and (b) wherein PKU affected hybridize to the mutant sequence, the PKU heterozygotes hybridize to both the mutant and normal sequences normals hybridize only to the normal sequence, and compound heterozygotes hybridize to two mutant sequences and the normal sequences.

3. A diagnostic kit effective for detecting a mutation in the human phenylalanine hydroxylase gene comprising:

(a) at least one oligonucleotide selected from the group specific to normal sequence of the human phenylalanine hydroxylase gene, specific to the mutant sequence of the human phenylalanine hydroxylase gene and any combination thereof;

(b) wherein at least one oligonucleotide of (a) hybridizes with target DNA from a source outside the kit to indicate the presence or absence of the mutant phenylalanine hydroxylase gene.

4. The diagnostic kit of claim 3 wherein the target DNA is human genomic material from fetal to adult individuals to be tested.

5. The diagnostic kit of claim 3 wherein:

(a) the mutant specific oligonucleotide sequence comprises at least one nucleotide sequence selected from the group consisting of: 5' . . . TCC ATT AAC AAT AAG TAA TTT . . . 3', 5' . . . AAA TTA CTT ATT GTT AAT GGA 3', 3' . . . CT CTT CCC GGT TCC ATA ACA C . . . 5' . . . C ACA ATA CCT CGG CCC TTC TC . . . 3' and 3' . . . G TGT TAT GGT GCC GGG AAG AG . . . 5'.

6. The diagnostic kit of claim 3 wherein:

(a) a pair of oligonucleotide sequences, one a mutant specific and the other a normal specific sequence are contained; (b) the paired sequences are selected from the group consisting of 5' . . . . TCC ATT AAC AAT AAG TAA TTT...3', 3' . . . AGG TAA TTG TCA TTC ATT AAA . . . 5', 5' . . . AAA TTA CTT ATT GTT AAT GGA 3', 3' . . . CT CTT CCC GGT TCC ATA ACA C . . . 5' and 3' . . . G TGT TAT GGA ACC GGG AAG AG . . . 5', 5' . . . C ACA ATA CCT CGG CCC TTC TC . . . 3', 3' . . . G TGT TAT GGT GCC GGG AAG AG...5' and 5' . . . TCC ATT AAC AGT AAC TAA TTT . . . 3' and any combination thereof.

7. A method of detecting a mutation in a phenylalanine hydroxylase gene of human genomic DNA comprising:
   (a) isolating a phenylalanine hydroxylase clone from a genomic DNA library with a human phenylalanine hydroxylase cDNA probe;
   (b) subcloning the phenylalanine hydroxylase gene;
   (c) sequencing the gene to define the mutation;
   (d) synthesizing an oligonucleotide sequence selected from a group consisting of an oligonucleotide complimentary to the mutated sequence and an oligonucleotide of the sense-strand of the mutated sequence;
   (e) synthesizing an oligonucleotide sequence selected from a group consisting of an oligonucleotide complimentary to the normal sequence and an oligonucleotide of the sense-strand of the normal sequence corresponding to the mutated sequence;
   (f) hybridizing the synthesized oligonucleotide of (d) and (e) to target DNA; and
   (g) identifying the hybridization fragments of step (f).

8. A method of detecting a mutation in a phenylalanine hydroxylase gene of human genomic DNA comprising:
   (a) isolating a phenylalanine hydroxylase clone from a genomic DNA library with a human phenylalanine hydroxylase cDNA probe;
   (b) subcloning the phenylalanine hydroxylase gene;
   (c) sequencing the gene to define the mutation;
   (d) isolating an oligonucleotide sequence selected from a group consisting of an oligonucleotide complimentary to the mutated sequence and an oligonucleotide of the sense-strand of the mutated sequence;
   (e) isolating an oligonucleotide sequence selected from a group consisting of an oligonucleotide complimentary to the normal sequence corresponding to the mutated sequence;
   (f) hybridizing the isolated oligonucleotide of (d) and (e) to target DNA; and
   (g) identifying the hybridization fragments of step (f).

9. A method of detecting PKU affected, PKU heterozygotes and normals in fetal to adult human samples comprising:
   detecting linkage of restriction endonuclease site in the phenylalanine hydroxylase gene.

10. The method of claim 9 where the restriction site is DdeI in exon 6 codon 232.

11. An automated method of detecting PKU affected, PKU helerozgotes and normals in fetal to adult human samples
   (a) amplification in vitro of phenylalanine hydroxylase mutations;
   (b) detection of the amplified mutations by hybridization with specific oligonucleotide probes for normal and mutant phenylalanine hydroxylase; and
   (c) determining the binding of the specific nucleotide probes wherein PKU affected hybridize to the mutant probe, the PKU heterozygotes hybridize to both the mutant and the normal probes and normals hybridize only to the normal probe, and compound heterozygotes hybridize to two mutant sequences and the normal sequences.

* * * * *

UNITED STATES PATENT OFFICE
CERTIFICATE OF CORRECTION

Patent No. 4,965,190  Dated October 23, 1990

Inventor(s) Savio L. C. Woo; Anthony G. Dilella

It is certified that error appears in the above-identified patent and that said Letters Patent is hereby corrected as shown below:

Column 1, line 15, after "such" add -- patients were unable to convert phenylalanine to tyrosine, --

Column 7-8, Table 2, last column heading, after "HAPLOTYPE 3" change "MUTANT" to -- NORMAL --

Column 9, line 68, change "5-donor" to -- 5'-donor --

Column 10, line 45, before "containing" change "allel" to -- allele --

Column 12, line 19, change "5 portion" to -- 5' portion --

Column 12, line 41, after "74," change "463" to -- 5463 --

Column 12, line 50, before "for" change "Cessed" to -- cessed --

Column 13, line 32, after "sequence" change "ca" to -- can --

Column 14, line 27, after "C-A" change "mismatCh" to -- mismatch --

UNITED STATES PATENT AND TRADEMARK OFFICE
CERTIFICATE OF CORRECTION

PATENT NO. : 4,965,190

DATED : October 23, 1990

INVENTOR(S) : Savio L. C. Woo

It is certified that error appears in the above-identified patent and that said Letters Patent is hereby corrected as shown below:

Column 20, line 59, after "C...5'" add --, and 3'...G TGT TAT GGA ACC GGG AAG AG...5'; and (b) the normal specific oligonucleotide sequence comprises at least one nucleotide sequence corresponding to the sequence in (a) selected from the group consisting of 3'... AGG TAA TTG TCA TTC ATT AAA...5', 5'...TCC ATT AAC AGT AAC TAA TTT... 3' and 5' --

Column 22, line 20, after "restriction" add -- endonuclease

Column 22, line 23, after "PKU" change "helerozgotes" to --heterozgotes --

Column 22, line 24, after "samples" add -- comprising: --

Signed and Sealed this

Tenth Day of March, 1992

Attest:

HARRY F. MANBECK, JR.

*Attesting Officer*     *Commissioner of Patents and Trademarks*